United States Patent [19]

Watts, Jr. et al.

[11] 4,148,802

[45] Apr. 10, 1979

[54] METHOD OF PREPARING ALPHA-VINYLOXAZOLINES

[75] Inventors: Lewis W. Watts, Jr.; Ernest L. Yeakey, both of Austin, Tex.

[73] Assignee: Texaco Development Corp., White Plains, N.Y.

[21] Appl. No.: 892,521

[22] Filed: Apr. 3, 1978

Related U.S. Application Data

[63] Continuation-in-part of Ser. No. 723,421, Sep. 15, 1976, abandoned.

[51] Int. Cl.$^2$ ............................................. C07D 263/12
[52] U.S. Cl. ................................................... 260/307 F
[58] Field of Search ...................................... 260/307 F

[56] References Cited

U.S. PATENT DOCUMENTS

| | | | |
|---|---|---|---|
| 3,962,270 | 6/1976 | Arlt | 260/307 F |
| 3,979,405 | 9/1976 | Toth et al. | 260/307 F |

OTHER PUBLICATIONS

March, "Advances in Organic Chemistry: Reactions, Mechanisms and Structure", McGraw Hill, N. Y., (1968), p. 755.

Adams et al., "Organic Reactions", vol. V, John Wiley & Sons, Inc., N. Y., (1949), p. 89.

*Primary Examiner*—Raymond V. Rush
*Attorney, Agent, or Firm*—Carl G. Ries; Thomas H. Whaley; James L. Bailey

[57] ABSTRACT

Covers a method of preparing an alpha-vinyloxazoline compound from the corresponding oxazoline ether compound, and more preferably covers a three step synthesis of preparing alpha-vinyloxazolines via reaction of acrylonitrile and alcohols.

6 Claims, No Drawings

METHOD OF PREPARING ALPHA-VINYLOXAZOLINES

REFERENCE TO RELATED DISCLOSURE

This application is a continuation-in-part of copending application Ser. No. 723,421, filed Sept. 15, 1976 now abandoned.

BACKGROUND OF THE INVENTION

1. Field of the Invention

This invention pertains to the field of preparing nitrogen heterocycles, and more particularly to oxazolines having an alpha-vinyl group attached thereto.

2. Description of the Prior Art

Vinyloxazolines are valuable commercial products useful in a wide variety of application areas particularly where materials of this type are utilized as monomers or co-monomers. However, many prior art processes of making compounds of this type employ relatively expensive reagents and/or reactants not readily available. In other cases, while the reaction scheme is operable, the sought-after vinyloxazoline product during isolation is polymerized or the ring compound is broken, and thus the desired monomer is not isolatable in good yields.

It has now been discovered that alpha-vinyloxazolines can now be synthesized in good yields from relatively inexpensive reagents via a synthetic scheme which does not cause polymerization and/or product breakdown through ring opening.

SUMMARY OF THE INVENTION

The present invention is concerned with a method or preparing an alpha-vinyloxazoline having the structural formula:

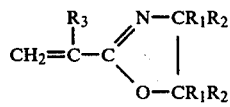

where $R_1$ and $R_2$ individually represent hydrogen, methyl or ethyl and $R_3$ is hydrogen or a $C_1$–$C_4$ lower alkyl radical, which comprises the step of providing an oxazoline ether compound having the structural formula:

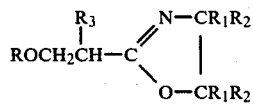

where R is $C_1$–$C_4$ lower alkyl and $R_1$, $R_2$ and $R_3$ are as stated above and treating said oxazoline ether compound with a strong base selected from the group consisting of alkali metal hydrides, alkoxides and hydroxides to provide said alpha-vinyloxazoline.

DESCRIPTION OF THE PREFERRED EMBODIMENTS

To carry out the process of the invention in its broadest aspects there is first provided an oxazoline ether compound falling within the above structural formula where R, $R_1$, $R_2$ and $R_3$ have the above-mentioned significance. The $C_1$–$C_4$ lower alkyl groups, R and $R_3$ may thus be methyl, ethyl, isopropyl, n-propyl, isobutyl, n-butyl, and t-butyl.

The strong base catalysts which may be employed here include alkali metal hydrides, alkoxides and hydroxides. Thus, sodium, potassium, and lithium compounds of this type may be employed. When an alkoxide is employed, it is preferred that the alkyl group be $C_1$–$C_4$ lower alkyl of the type discussed with reference to radicals R and $R_3$. A preferred alkoxide is an alkali metal methoxide such as sodium methoxide. The catalyst may be used in any desired amount. Typically, the amount of catalyst employed may range from about one percent to about thirty percent based on the weight of the starting oxazoline ether compound.

The formation of the vinyloxazoline from the corresponding ether compound again may be effected over a wide temperature range. Usually, the temperature of reaction ranges from about 0° C. to about 220° C., and more often is 50–200° C.

The reaction may be run in the presence or absence of solvent. It is preferred that when a solvent is employed a high boiling material be used, inert to both the reactant and product. Thus, for example, high boiling ethers, and hydrocarbons may be used here. Specific examples include decalin and trimethylbenzene. Other materials useful as solvents include diphenyl ethers and biphenyl itself.

The reaction may be run under atmospheric pressure conditions or sub-atmospheric. The latter is preferred since one then can immediately isolate from the reaction mass the product as formed by distilling therefrom.

It is interesting to note that other catalytic systems were attempted here and failed. For example, a number of acid catalysts were tried in attempts to produce the vinyloxazoline from the corresponding ether oxazoline, but without success in isolating the desired vinyl product in any appreciable yield. Yet, when the process of the invention was followed as outlined here, the vinyl product was recovered in excellent yields. Through use of the scheme here, the vinyloxazoline could be recovered without substantial polymerization occurring and/or undesirable ring opening. With respect to avoidance of polymerization, an inhibitor such as phenothizaine may be present during the reaction, though its presence is not critical in this regard.

In a greatly preferred scheme, the starting oxazoline ether compounds are produced in the following manner. Specifically, relatively inexpensive reagents are first provided comprising acrylonitrile or a substituted acrylonitrile of the formula $CH_2=CR_3CN$ where $R_3$ is a $C_1$–$C_4$ lower alkyl radical and a lower alkyl monohydroxylic alcohol, ROH, where R is as above. These materials are reacted to provide a nitrile having the following structural formula:

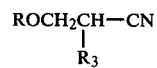

This nitrile in turn is reacted with a monoalkanol-amine having the formula:

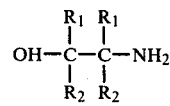

where $R_1$ and $R_2$ are hydrogen, methyl or ethyl radicals. This condensation reaction in turn then provides the oxazoline ether compound, which is thus transformed into the vinyloxazoline by base catalysis as outlined above.

The following examples illustrate typical modes of carrying out the process of the invention. It is understood, of course, that these examples are merely illustrative and that the invention is not to be limited thereto.

EXAMPLE I

Into a small distillation flask was charged 13.0 grams of the oxazoline derivative having the formula

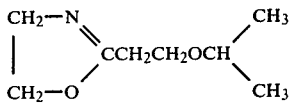

0.3 grams anhydrous sodium methoxide, and approximately 0.2 grams of phenothizaine. The resultant mixture was heated under reduced pressure (70 mm Hg) and an initial overhead fraction was isolated which proved to be primarily isopropanol. A second fraction was then obtained which consisted of a mixture of isopropanol and alpha-vinyloxazoline.

EXAMPLE II

The procedure of Example I was followed with the exception that a $C_{14}$ alcohol was employed as a solvent. By heating 10 grams of the ether oxazoline of Example I in presence of about 3 grams sodium methoxide up to a temperature of 170° C. at sub-atmospheric pressures, there was isolated 4.7 grams of a mixture of isopropanol and alpha-vinyloxazoline.

EXAMPLE III

Here a preferred synthesis of alpha-vinyloxazoline was carried out as follows.

To a solution of isopropanol (1360 grams, 22.67 moles) and sodium methoxide-methanol (20 ml. of a 25 weight percent solution of sodium methoxide in methanol), there was added dropwise at 45–65° C., 750 grams (14.15 moles) of acrylonitrile. Upon completion of the addition, the resulting mixture was first warmed to 75° C. for one hour, acidified to a pH of 2 with concentrated HCl, and then adjusted to a pH of 7 with ammonium hydroxide. The reaction mixture was then filtered and vacuum distilled and the desired adduct

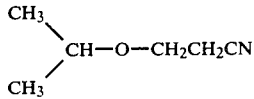

was isolated in a 75.7 percent yield.

The above nitrile, beta-isopropoxypropionitrile, in an amount of 56.6 grams was added along with 30.0 grams of monoethanolamine, to 2.5 grams of cadmium acetate. The mixture was warmed at 110° C. for approximately 14 hours. The resultant crude reaction mixture was then vacuum distilled producing 76 grams overhead containing the derivative having the structure:

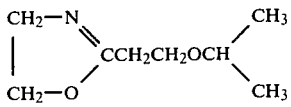

5.5 grams of the ether oxazoline above was mixed with 0.1 grams of sodium hydroxide and 0.1 grams of phenothizaine. The mixture was slowly heated to 90° C. at 35 mm. Hg pressure. The overhead material in an amount of 5.1 grams was collected which consisted of starting material, vinyloxazoline, and isopropanol in a molar ratio of 1:6.4:6.0.

We claim:

1. A method of preparing an alpha-vinyloxazoline having the structural formula:

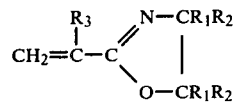

where $R_1$, and $R_2$ individually represent hydrogen, methyl or ethyl radicals and $R_3$ is hydrogen or a $C_1$–$C_4$ lower alkyl radical which comprises the step of providing an oxazoline ether compound having the structural formula:

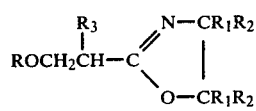

where R is $C_1$–$C_4$ lower alkyl and $R_1$, $R_2$ and $R_3$ are as stated above and treating said oxazoline ether compound with a strong base selected from the group consisting of alkali metal hydrides, alkoxides containing 1–4 carbon atoms and hydroxides at a temperature ranging from about 0° C. to about 220° C. to provide said alpha-vinyloxazoline.

2. The method of claim 1 wherein said temperature range is 50–200° C.

3. The method of claim 1 wherein $R_1$ and $R_2$ are hydrogen.

4. The method of claim 1 wherein said strong base is sodium methoxide.

5. The method of claim 1 wherein R is isopropyl.

6. A method of preparing an alpha-vinyloxazoline having the structural formula:

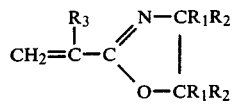

where $R_1$ and $R_2$ individually represent hydrogen, methyl or ethyl radicals and $R_3$ is hydrogen or a lower $C_1$–$C_4$ alkyl radical which comprises the steps of reacting acrylonitrile or a substituted acrylonitrile of the formula $CH_2\!=\!CR_3CN$ where $R_3$ is as above with a lower alkyl monohydroxylic alcohol to provide a nitrile having the following structural formula:

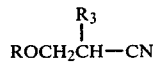

where R is $C_1$–$C_4$ lower alkyl, reacting said nitrile with a monoalkanol-amine having the formula:

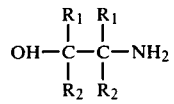

where $R_1$ and $R_2$ are as above to provide an oxazoline ether compound having the structural formula:

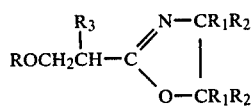
where R, R₁, R₂ and R₃ are as stated above and treating said oxazoline ether compound with a strong base selected from the group consisting of alkali metal hydrides, alkoxides containing 1-4 carbon atoms and hydroxides at a temperature ranging from about 0° C. to about 220° C. to provide said alpha-vinyloxazoline.